US012658070B2

(12) United States Patent
Nishiura

(10) Patent No.: US 12,658,070 B2
(45) Date of Patent: Jun. 16, 2026

(54) SYSTEM FOR SUPPORTING MEAL MENU DESIGNING

(71) Applicant: Ryutaro Nishiura, Tokyo (JP)

(72) Inventor: Ryutaro Nishiura, Tokyo (JP)

( * ) Notice: Subject to any disclaimer, the term of this patent is extended or adjusted under 35 U.S.C. 154(b) by 1140 days.

(21) Appl. No.: 17/053,172

(22) PCT Filed: Apr. 12, 2019

(86) PCT No.: PCT/JP2019/016045

§ 371 (c)(1),
(2) Date: Nov. 5, 2020

(87) PCT Pub. No.: WO2019/216124

PCT Pub. Date: Nov. 14, 2019

(65) Prior Publication Data

US 2021/0241653 A1 Aug. 5, 2021

(30) Foreign Application Priority Data

May 7, 2018 (JP) ................................. 2018-089140
Jun. 19, 2018 (JP) ................................. 2018-116017

(51) Int. Cl.
*G09B 19/00* (2006.01)
*G16H 20/40* (2018.01)
*G16H 20/60* (2018.01)

(52) U.S. Cl.
CPC ......... *G09B 19/0092* (2013.01); *G16H 20/40* (2018.01); *G16H 20/60* (2018.01)

(58) Field of Classification Search
CPC ................................................ G09B 19/0092
See application file for complete search history.

(56) References Cited

U.S. PATENT DOCUMENTS

| | | | |
|---|---|---|---|
| 5,704,350 A * | 1/1998 | Williams, III | G16H 70/00 |
| | | | 600/300 |
| 12,094,016 B2 * | 9/2024 | Yahata | G06Q 30/0635 |
| 2010/0136508 A1 * | 6/2010 | Zekhtser | G16H 20/60 |
| | | | 434/127 |

(Continued)

FOREIGN PATENT DOCUMENTS

| | | |
|---|---|---|
| CN | 103577671 A | 2/2014 |
| CN | 104112060 A | 10/2014 |

(Continued)

OTHER PUBLICATIONS

International Search Report issued in corresponding PCT Application No. PCT/JP2019/016045 dated Jul. 9, 2019, 3 pages.

(Continued)

*Primary Examiner* — Eugene L Kim
*Assistant Examiner* — Alyssa M Hylinski
(74) *Attorney, Agent, or Firm* — DILWORTH IP, LLC

(57) ABSTRACT

A terminal includes a display configured to display a plurality of options of food and/or beverage; an identifying unit configured to identify food and/or beverage selected by a user from the plurality of options; a presenting unit configured to present food and/or beverage to be ingested together with the selected food and/or beverage; and a determining unit configured to determine a dietary menu from the presented food and/or beverage including the specified food and/or beverage.

11 Claims, 4 Drawing Sheets

(56) References Cited

U.S. PATENT DOCUMENTS

| | | | | |
|---|---|---|---|---|
| 2011/0123964 A1* | 5/2011 | Aronis | .................... | G16H 20/60 434/127 |
| 2011/0143322 A1* | 6/2011 | Tsang | ..................... | G16H 20/30 434/127 |
| 2012/0096405 A1* | 4/2012 | Seo | ......................... | G16H 20/60 715/825 |
| 2013/0216982 A1* | 8/2013 | Bennett | ................ | A61B 5/4866 434/127 |
| 2014/0315160 A1* | 10/2014 | Hayashi | ............. | G09B 19/0092 434/127 |
| 2015/0103677 A1* | 4/2015 | Lee | ..................... | H04L 41/0896 370/249 |
| 2015/0212661 A1* | 7/2015 | Robberechts | ....... | G07F 17/0064 715/810 |
| 2017/0103677 A1* | 4/2017 | Bhattacharjee | ........ | G16H 20/70 |
| 2017/0316488 A1* | 11/2017 | Kremen | .................... | G09B 5/06 |
| 2017/0352289 A1* | 12/2017 | Israetel | ............. | G01G 23/3735 |
| 2018/0374386 A1* | 12/2018 | Benefield | ........... | A63B 24/0059 |
| 2019/0080629 A1* | 3/2019 | Gopalan | ................ | G16H 40/63 |

FOREIGN PATENT DOCUMENTS

| | | |
|---|---|---|
| JP | 2001312563 A | 11/2001 |
| JP | 2014211749 A | 11/2014 |
| JP | 2016200963 A | 12/2016 |
| WO | 2014129205 A1 | 2/2017 |

OTHER PUBLICATIONS

Second Notification of Office Action issued in Chinese Patent Application No. 201980000824.X, issued on May 20, 2023.
Office Action issued by the CNIPA in corresponding Chinese Patent Application No. 201980000824.X, dated Dec. 5, 2022.
Third Notification of Office Action issued in Chinese Patent Application No. 201980000824.X, dated Sep. 1, 2023.

* cited by examiner

<SELECT DESIRED DISHES>
<SELECTABLE DISHES>
STEAK
FRIED VEGETABLES
GRILLED FISH
BOILED FISH
<NON-SELECTABLE DISHES>
RAMEN NOODLES
PORK CUTLET RICE
BOWL
Fig. 5
DIETARY AND EXERCISE
MENUS
1. LET'S HAVE A TOMATO
JUICE FIST.
2. ENJOY STEAK.
3.PLEASE HAVE RICE
LAST.
* EXERCISE FOR XXX KCAL
(CORRESPONDING TO A
WALK FOR XX KM)
Fig. 6

Fig. 7

SYSTEM FOR SUPPORTING MEAL MENU DESIGNING

TECHNICAL FIELD

The present invention relates to provision of a dietary menu.

BACKGROUND

Known is a technology for provision of a dietary menu. For example, Japanese Patent Publication No. JP2016-200963A discloses provision of a preferable dietary menu in consideration of an activity pattern and a food preference of a user.

In the method described in Japanese Patent Publication No. JP2016-200963A, the user follows the proposed dietary menu but is not actively involved in generation of the menu. In addition, even if a food preference of the user is taken into consideration in preparation of the proposed dietary menu, the user may be restricted from eating a desired food. As a result of not being able to eat a desired food, user stress accumulates, and concomitantly there is a decrease in nutrition-management motivation. An object of the present invention is to determine a nutritionally appropriate dietary menu while actively involving the user in generating the menu.

SUMMARY OF THE INVENTION

In an embodiment, the present invention provides a device that includes a display unit for displaying a plurality of food and/or beverage options, an identifying unit configured to specify food and/or beverage selected by a user from among the options, a presenting unit configured to present food and/or beverage to be ingested together with the selected food and/or beverage, and a determining unit configured to determine a dietary menu from the presented food and/or beverage including the selected food and/or beverage.

The dietary menu may contain information on an order of ingestion of the food and/or beverage.

The device may execute a step of inputting into the determined dietary menu an ingested meal, and a step of adjusting a number of options based on the input meal; a step of generating a plan for management of physical healthcare of the user, and a step of judging a level of achievement of the plan based on meals ingested multiple times, and changing the plan based on the level; a step of inputting an amount of physical activity performed by the user, and adjusting the number of options based on the meals ingested and the amount of physical activity performed; a step of generating a plan for the management of physical healthcare of the user, and judging the level of achievement of the plan based on the meals ingested and the amount of physical activity performed within a time period.

According to the present invention a nutritionally appropriate dietary menu is determined while actively involving the user in generating a dietary menu.

BRIEF DESCRIPTION OF THE DRAWINGS

FIG. 5 shows an example of a screen of terminal 100, in accordance with the present invention.

FIG. 6 also shows an example of a screen of terminal 100, in accordance with the present invention.

FIG. 7 also shows an example of a screen of terminal 100, in accordance with the present invention.

DETAILED DESCRIPTION

Figure 1:
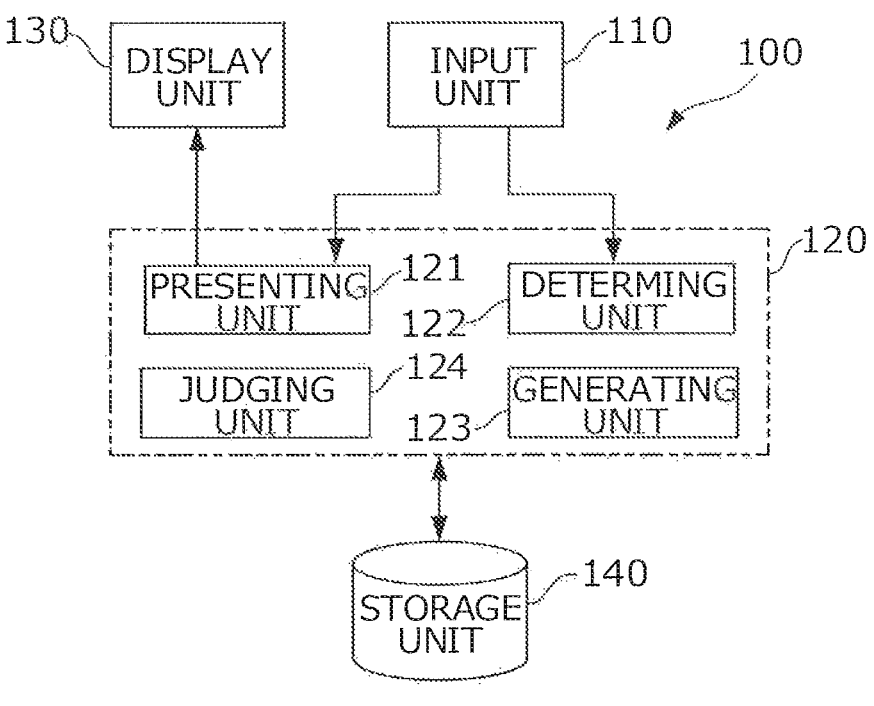
FIG. 1 shows a functional diagram of terminal 100, in accordance with the present invention.

FIG. 1 is a functional diagram of the terminal 100. The terminal 100 is a device that has an input and output function for display of information, such as a smartphone or a personal computer, and includes an input unit 110, an information processing unit 120, a display 130, and a storage unit 140.

The storage unit 140 is a storage device, such as a semiconductor memory, that realizes a function executed based on a user's instruction according to the present invention, as will be described later. In addition, a plan is stored for managing and improving physical healthcare of the user through ingestion of food (for example, a variety of information can be entered by the user, such as losing 3 kg of body weight within one month)—hereinafter referred to as a "physical management plan." Further, information is stored on the actual dietary content and physical activity input by the user, and a database including algorithms and information on nutrition and food and/or beverage is used by the information processing unit 120 to judge, suggest, or evaluate and generate a long-term or short-term advice.

The display unit 130 is a device that includes a liquid crystal panel and a processor for displaying information generated by the terminal 100. The display unit 130 displays food and/or beverage options. In addition, the display unit 130 displays a determined dietary menu, physical exercise plan, and a report on the status of progress of the physical management plan.

The input unit 110 is an input device such as a touch panel or a mouse, and receives input of information from the user. Specifically, the input unit 110 functions as a specifying unit for receiving the food and/or beverage selected by the user from among the plurality of options and specifying the selected food and/or beverage. The user inputs via the input unit 110 information on an amount of physical activity performed by the user. In addition, information is input via the input unit 110 on the user's physical management plan and information on a current physical condition of the user (height, weight, basal metabolic rate, etc.). The input unit 110 may have a communication function for connecting to an information device and acquiring the information. In this case, information on the amount of physical activity of the user may be obtained from an information device such as a pedometer (registered trademark) using the communication function.

The information processing unit 120 is a processor and includes a presenting unit 121, a determining unit 122, a generating unit 123, and a judging unit 124. The presenting unit 121 presents the food and/or beverage to be ingested together with the food and/or beverage selected by the user. In a preferred embodiment, the presenting unit 121 adjusts a number of options based on a meal ingested and an amount of physical activity performed.

The determining unit 122 determines a dietary menu from the presented food and/or beverage that includes the selected food and/or beverage. The dietary menu may include information on the order of ingestion, as well as the type of food and/or beverage. Namely, the determined dietary menu necessarily includes the food and/or beverage selected by the user.

The generating unit 123 generates a physical management plan for the user. For example, the plan is defined by factors such as a body weight, body fat, muscle-mass, and bone density to be increased or decreased. As an example, the Harris-Benedict method is used to calculate the basal metabolic rate based on physical information, and based on the target physical condition (body weight, etc.), the period until the target is achieved, and the set amount of exercise, a difference between the calories ingested and the calories consumed for each meal is calculated.

The Judging unit 124 determines a level of achievement of the plan based on the content of the plurality of meals ingested a plurality of times and/or the amount of physical activity performed by the user within a certain time period. The level of achievement may be defined, for example, by the ratio of a weight at a time according to the plan and a weight actually measured at the time.

Figure 2:
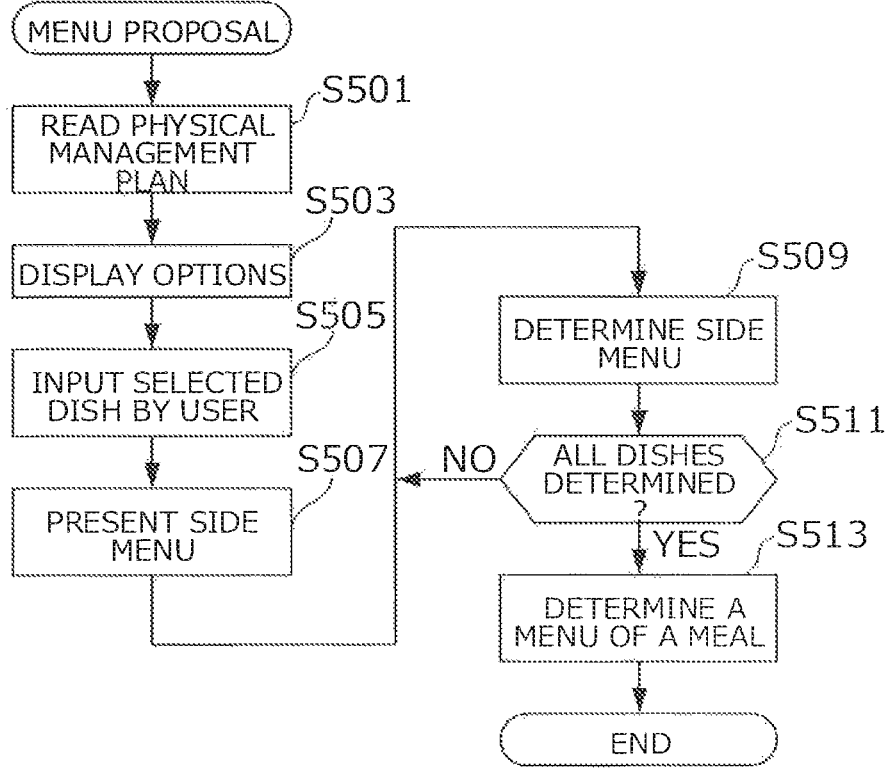
FIG. 2 shows an example of operation of terminal 100, in accordance with the present invention.

FIG. 2 shows an example operation of the terminal 100 in determining a dietary menu. The terminal 100 reads a current physical condition (body weight, amount of muscle, etc.) and the physical management plan (S501). The terminal 100 determines options and displays the options based on the read physical condition and the physical management plan (S503). FIG. 5 shows an example of a screen displaying the options. In this example, it is shown that steak, stir-fried vegetables, grilled fish, and boiled fish can be selected.

It is of note that ingredients and/or cooking methods may be selected instead of merely a finished product. In addition, the options may be hierarchized such as "meat"→ "beef"→"stir-fried beef." By presenting elements of a dish in a hierarchical order, a dish included in the options can be finalized by selecting the elements of the dish two or more times.

Returning to FIG. 2, the terminal 100 accepts the user's selection (S505). For example, in the example shown in FIG. 5, steak is selected. Subsequently, the terminal 100 refers to the stored physical management plan and information on the nutrition stored in the database, and presents one or more side dishes and the order of eating that is suitable for the selected steak (S507). When two or more options are presented, the terminal 100 accepts the selection made by the user and determines a single dish to be eaten (S509). In a case where two or more dishes are proposed, all dishes are determined (S511). In this way, the terminal 100 determines the menu for a meal (S513). The determined dietary menu is displayed on the screen. FIG. 6 is an example of a screen at this time. In this example, a dietary menu is proposed in which the selected steak is first ingested together with tomato juice, which is preferable with respect to lipolytic activity and vitamin content, and carbohydrates being ingested at the end.

Figure 3:
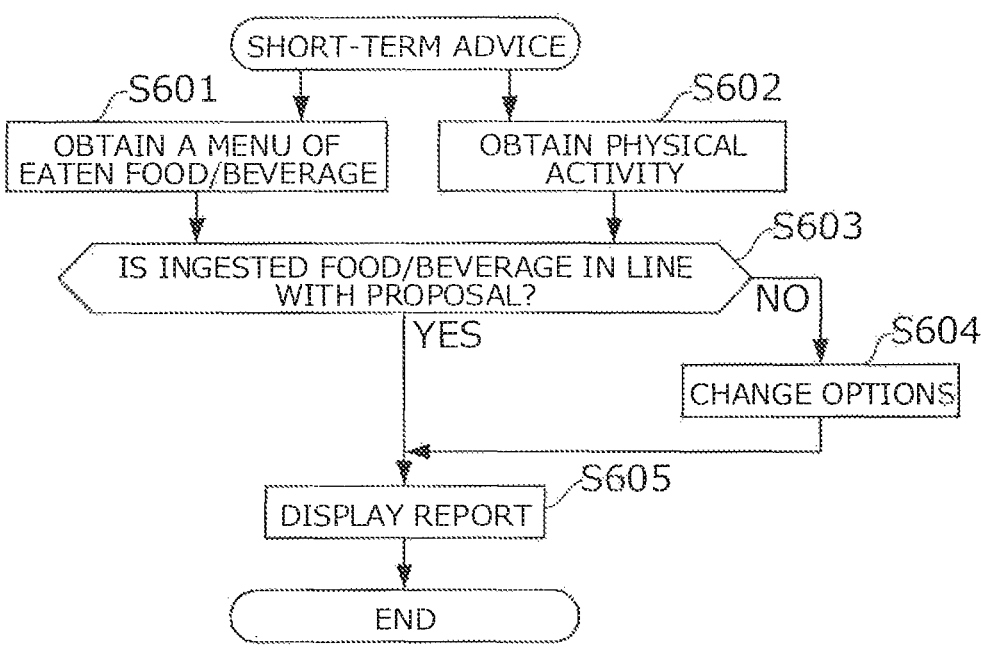
FIG. 3 also shows an example of operation of terminal 100, in accordance with the present invention.

FIG. 3 shows an example operation for generating short-term advice. The terminal 100 acquires a report of a meal at a predetermined time (for each meal or for one day, or when a predetermined period has elapsed since the last start of the application program, etc.) in S601. In addition, the amount of physical activity performed may be acquired if necessary (S602). It is preferable to also acquire information on a current physical condition (body weight, etc.). Specifically, when a predetermined time arrives, a message prompting the user to input information is displayed on the screen.

Based on the acquired information, the terminal 100 determines whether the meal was eaten in accordance with the proposed dietary menu and whether exercise was performed according to the proposal (S603). As a result of the determination, if a difference between the proposed dietary menu and the actual meal and/or physical activity is greater than or equal to a reference threshold, the option is changed (S604). The change is reflected in the screen display when a dietary menu for the next meal is proposed. If the difference is less than the reference threshold, the options are maintained. Subsequently, the terminal 100 generates a report including an evaluation with regard to a meal ingested and exercise performed, and advice on future diet and exercise, and displays the report on the screen (S605).

Figure 7:
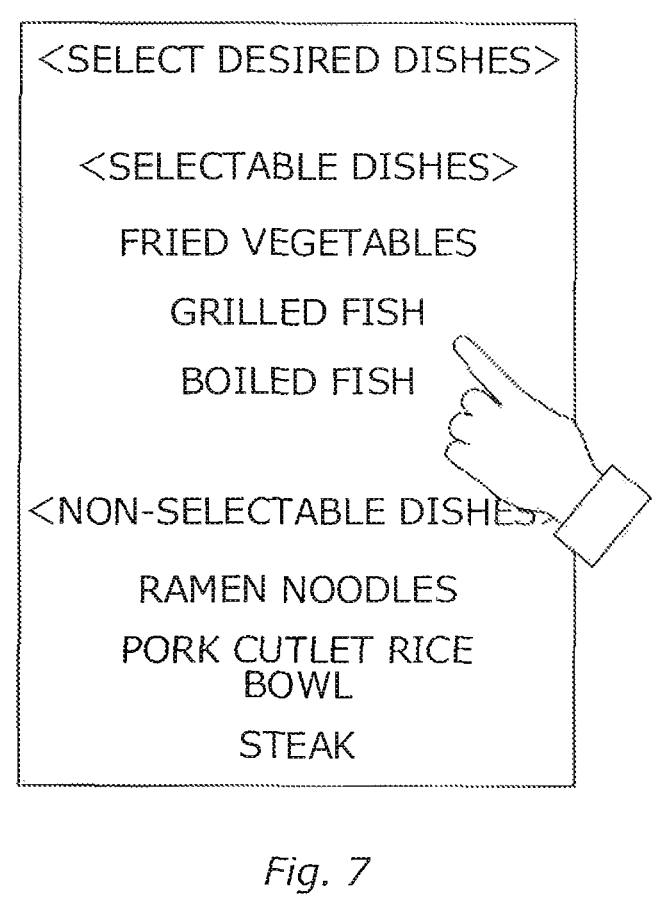

FIG. 7 is an example of a screen that is displayed when proposing the next dietary menu when the options are changed. Unlike in FIG. 5, it is not possible to select the steak, which is a relatively high-calorie food, because the meal the user ingested exceeds the calorie limit and/or the amount of exercise performed is insufficient. Namely, the choices are reduced because diet or exercise that the user followed is unfavorable. On the contrary, if the diet and exercise followed by the user are as expected or are greater than expected, the options will be maintained or increased.

Figure 4:
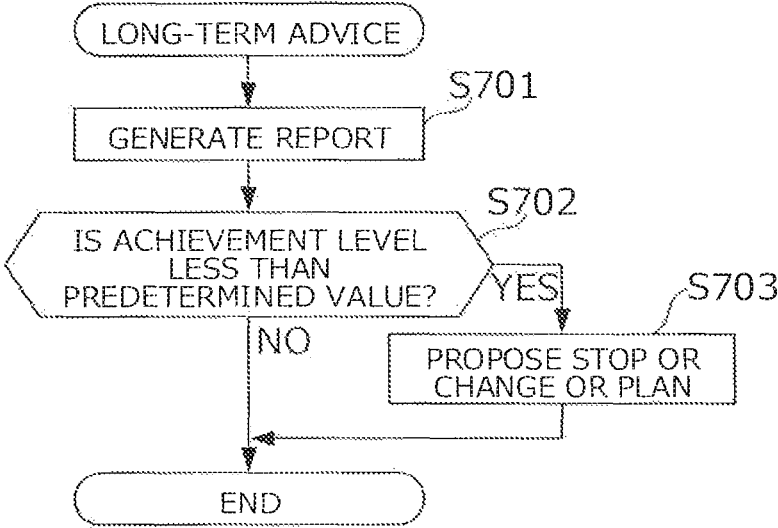
FIG. 4 shows an example of operation of terminal 100, in accordance with the present invention.

FIG. 4 is an example operation for providing long-term advice. The terminal 100 periodically generates a report on the progress of the physical management plan when a predetermined number of meals (for example, 10 meals) or a predetermined number of days (for example, one week) has passed from the first day of starting the physical management plan or the number of options is less than a predetermined value (S701). The report includes information on a level of achievement of the plan and/or a level of divergence between the plan and the performance (simply referred to as "achievement"). Specifically, the terminal 100 calculates the level of achievement based on the accumulated history of the user's physical condition and history of diet and exercise and the physical management plan.

Next, the terminal 100 determines whether the current achievement (for example, the level of deviation from the target value with respect to a period of time remaining for accomplishing the plan is equal to or less than the predetermined value (S702). If the current achievement is equal to or less than the predetermined value (S702: YES), the terminal 100 proposes cancellation or change (review) of the plan (S703). If the terminal 100 decides to change the plan, the terminal 100 generates a revised plan. If the achievement level is not below the specified value (in other words, the dietary menu is being executed as planned), the plan will not be changed.

According to the above embodiment, the user is firstly given the right to select a dish that the user wishes to have, and then another dish(es) that is appropriate in conjunction with the selected dish are proposed. As a result, a dietary menu appropriate for physical management or nutritional management is proposed while allowing the user to have his-her favorite food and/or beverage in as far as possible. Since it is ensured that the user is able to have whatever food and/or beverage he/she wishes within the proposed choices, the user is not likely to feel constrained by forced decisions on a dietary menu. Rather, the user is empowered by being proactively involved in the plan.

In addition, it is determined whether the user had meals and/or performed exercise in accordance with the proposed plan based on a meal(s) that the user had (and optionally on information on physical activity performed), and a choice of dishes available to the user changes based on the determination result. Specifically, if the user has not had food and/or beverage as suggested, the user has less freedom of choice, and conversely if the user has eaten food and/or beverage as suggested (or better than suggested), freedom of choice is maintained or increased. In other words, since meals that the user has had and exercise that the user performed are fed back with a greater freedom of choice thereby being provided to the user, consciousness motivation to proactively participate in physical management is enhanced, and thus a possibility of attaining a desired goal can be expected to increase.

In addition, in a case where deviation from the goal (feasibility) deteriorates to a certain level and as a consequence no desired food and/or beverage options are available for choice, abandonment or change of the current physical management plan is proposed. This allows the user to look back at the physical management thus far and motivates the user to reset his/her goal at an opportune time. As a result, it is possible to prevent the user from losing motivation in managing his/her physical healthcare.

Information such as an image of cooked dishes, a moving image of a recipe, a commentary or the like may also be displayed on the screen when displaying the options or the determined menu.

The function of determining food and/or beverage, the function of determining a dietary menu and physical activity, and the function of generating a report may be performed by a server (not shown in the figures) that communicates with the terminal 100. Namely, in a method of proposing a dietary menu according to the present invention, displaying options of food and/or beverage, determining food and/or beverage to be ingested together with the food and/or beverage selected by the user from the options, and presenting food and/or beverage are executed by one or more information processing devices.

REFERENCE NUMERALS

100 terminal
110 input unit
120 information processing unit
130 display
140 storage unit
121 presentation unit
122 determination unit
123 generation unit
124 judging unit

The invention claimed is:

1. A device comprising:
a display configured to display a plurality of options of food or beverages; and
a processor configured to:
identify a first food or beverage for a first meal selected by a user operating an input device from the plurality of options on the display;
present on the display a second food or beverage to be selected by the user with the input device from the plurality of options and ingested together with the selected first food or beverage in the first meal;
wherein the display is further configured to display a first dietary menu for the first meal including the selected first food or beverage and the selected second food or beverage;

the processor further configured to:
generate and store in a storage device a plan for physical management of the user to achieve a target physical condition in a period until the target is achieved;
acquire content of a meal ingested by the user and an amount of physical activity performed by the user and store the acquired content in the storage device as a history of the user's diet and exercise in performing the plan;
acquire nutrition information stored in the storage device on the food or beverage of the ingested meal;
calculate calories of the ingested meal and calories consumed by the physical activity performed by the user;
calculate a ratio of a target weight at a time according to the plan for the user and a weight of the user as actually measured at the time and define a level of achievement of the plan for the user as the calculated ratio; and
determine a next dietary menu appropriate to achieve the target physical condition for a next meal, wherein the next meal incudes a next first and a next second food or beverage selectable by the user from the plurality of options of food or beverages displayed on the display based on the level of achievement of the target physical condition;
wherein when at least one of the meal ingested by the user exceeds a calorie threshold or the physical activity performed by the user is less than an activity threshold, the processor reduces the plurality of options of foods or beverages displayed on the display that are selectable by the user for the next first and the next second food or beverage by preventing selection by the user operating the input device of food or beverages displayed on the display that do not achieve the target physical condition; and
wherein when at least one of the meal ingested by the user is less than or equal to the calorie threshold or the physical activity performed by the user is greater than or equal to the activity threshold, the processor at least one of maintains or increases the plurality of options of foods or beverages displayed on the display that are selectable by the user for the next first and the next second food or beverage by allowing selection by the user operating the input device of the food or beverages displayed on the display that achieves the target physical condition;
thereby actively involving the user in generating a nutritionally appropriate dietary menu to achieve the user's target physical condition according to the plan.

2. The device according to claim 1, wherein the next dietary menu includes information on an order of ingestion of food or beverage.

3. The device according to claim 1, wherein:
the input device is operable by the user to input the next meal ingested by the user.

4. The device according to claim 3, wherein the processor is further configured to:
determine and judge a current level of achievement of the plan and a level of divergence between the plan and the performance of the user based on an accumulation of history of the user's physical condition and of a history of a plurality of meals that has been ingested and the physical activity performed by the user, and when the current level of achievement is one of equal to or less than a predetermined value changing the plan based on the judged levels by generating a revised plan.

5. The device according to claim 4, wherein:

the input device is operable by the user to input the amount of the physical activity performed by the user.

6. The device according to claim 5, wherein the current level of achievement of the plan is periodically determined based on the accumulation of history of the user's physical condition and of the history of the plurality of meals ingested and the amount of physical activity performed within a time period, and wherein the processor is further configured to generate and to present on the display a report on the user's progress under the plan during the time period.

7. The device according to claim 1, wherein the plan for physical management of the user includes factors of body weight, body fat, muscle-mass, and bone density, the factors to be increased or decreased for the user.

8. The device according to claim 1, wherein the plurality of options of food or beverage displayed on the display includes ingredients and cooking methods.

9. The device according to claim 1, wherein the plurality of options of food or beverages displayed on the display includes non-selectable food or beverages together with selectable food or beverages to motivate the user to proactively participate in the plan.

10. A non-transitory computer readable storage medium that stores a program causing a computer to execute:

displaying on a display a plurality of options of food or beverages;

identifying a first food or beverage for a first meal selected by a user operating an input device from the plurality of options displayed on the display;

presenting on the display a second food or beverage to be selected by the user with the input device from the plurality of options and ingested together with the selected first food or beverage in the first meal;

displaying to the user a first dietary menu for the first meal including the selected first food or beverage and the selected second food or beverage;

generating and storing in a storage device a plan for physical management of the user to achieve a target physical condition in a period until the target is achieved;

acquiring content of a meal ingested by the user and an amount of physical activity performed by the user and store the acquired content in the storage device as a history of the user's diet and exercise in performing the plan;

acquiring nutrition information stored in the storage device on the food or beverage of the ingested meal;

calculating calories of the ingested meal and calories consumed by the physical activity performed by the user;

calculating a ratio of a target weight at a time according to the plan for the user and a weight of the user as actually measured at the time and defining a level of achievement of the plan as the calculated ratio; and determining a next dietary menu appropriate to achieve the target physical condition for a next meal, wherein the next meal includes a next first and a next second food or beverage selectable by the user from the plurality of options of food or beverages displayed on the display based on the level of achievement of the target physical condition;

wherein when at least one of the meal ingested by the user exceeds a calorie threshold or the physical activity performed by the user is less than an activity threshold, reducing the plurality of options of foods or beverages displayed on the display that are selectable by the user for the next first and the next second food or beverage by preventing selection by the user operating the input device of food or beverages displayed on the display that do not achieve the target physical condition; and wherein when at least one of the meal ingested by the user is less than or equal to the calorie threshold or the physical activity performed by the user is greater than or equal to the activity threshold, at least one of maintaining or increasing the plurality of options of foods or beverages displayed on the display that are selectable by the user for the next first and the next second food or beverage by allowing selection by the user operating the input device of the food or beverages displayed on the display that achieves the target physical condition;

thereby actively involving the user in generating a nutritionally appropriate dietary menu to achieve the user's target physical condition according to the plan.

11. A method of proposing a dietary menu, comprising:

displaying on a display a plurality of options of food or beverages;

specifying a first food or beverage for a first meal selected by a user operating an input device for a meal from the plurality of options on the display;

presenting on the display a second food or beverage to be selected by the user with the input device from the plurality of options and ingested for the meal together with the selected first food or beverage in the first meal;

displaying to the user on the display a first dietary menu for the first meal including the selected first food or beverage and the selected second food or beverage;

generating and storing in a storage device a plan for physical management of the user to achieve a target physical condition in a period until the target is achieved;

acquiring content of the meal ingested by the user and an amount of physical activity performed by the user and storing the acquired content in the storage device as a history of the user's diet and exercise in performing the plan;

acquiring nutrition information stored in the storage device on the food or beverage of the ingested meal;

calculating calories of the ingested meal and calories consumed by the physical activity performed by the user;

calculating a ratio of a target weight at a time according to the plan for the user and a weight of the user as actually measured at the time and defining a level of achievement of the plan for the user as the calculated ratio; and determining a next dietary menu appropriate to achieve the target physical condition for a next meal, wherein the next meal includes a next first and a next second food or beverage selectable by the user from the plurality of options of food or beverages displayed on the display based on the level of achievement of the target physical condition;

wherein when at least one of the meal ingested by the user exceeds a calorie threshold or the physical activity performed by the user is less than an activity threshold, reducing the plurality of options of foods or beverages displayed on the display thar are selectable by the user for the next first and the next second food or beverage by preventing selection by the user operating the input device of food or beverages displayed on the display that do not achieve the target physical condition; and wherein when at least one of the meal ingested by the user is less than or equal to the calorie threshold or the physical activity performed by the user is greater than or equal to the activity threshold, at least one of maintaining or increasing the plurality of options of foods or beverages displayed on the display that are selectable by the user for the next first and the next second food or beverage by allowing selection by the user with the input device of food or beverages displayed on the display that achieves the target physical condition;

thereby actively involving the user in generating a nutritionally appropriate dietary menu to achieve the user's target physical condition according to the plan.

\* \* \* \* \*